United States Patent
Yoda et al.

(10) Patent No.: US 11,879,135 B2
(45) Date of Patent: Jan. 23, 2024

(54) METHOD FOR DETERMINING UNDIFFERENTIATED STATE OF PLURIPOTENT STEM CELL, METHOD FOR SUBCULTURING PLURIPOTENT STEM CELL, AND DEVICE FOR USE IN THE METHODS

(71) Applicant: TOKYO ELECTRON LIMITED, Tokyo-to (JP)

(72) Inventors: Yusuke Yoda, Tokyo-to (JP); Kunitada Hatabayashi, Tokyo-to (JP); Kenichi Kagawa, Tokyo-to (JP)

(73) Assignee: TOKYO ELECTRON LIMITED, Tokyo-to (JP)

( * ) Notice: Subject to any disclaimer, the term of this patent is extended or adjusted under 35 U.S.C. 154(b) by 832 days.

(21) Appl. No.: 16/784,744

(22) Filed: Feb. 7, 2020

(65) Prior Publication Data
US 2020/0199529 A1 Jun. 25, 2020

Related U.S. Application Data

(63) Continuation of application No. PCT/JP2018/029770, filed on Aug. 8, 2018.

(30) Foreign Application Priority Data

Aug. 8, 2017 (JP) .................................. 2017-153679

(51) Int. Cl.
C12N 5/074 (2010.01)
C12M 1/00 (2006.01)
C12M 1/34 (2006.01)

(52) U.S. Cl.
CPC .......... C12N 5/0607 (2013.01); C12M 31/00 (2013.01); C12M 41/46 (2013.01)

(58) Field of Classification Search
None
See application file for complete search history.

(56) References Cited

U.S. PATENT DOCUMENTS

| 2006/0115804 A1 | 6/2006 | Hench et al. |
| 2017/0226558 A1 | 8/2017 | Hatabayashi et al. |
| 2017/0254741 A1 | 9/2017 | Suganuma et al. |
| 2019/0119650 A1 | 4/2019 | Suzuki et al. |

FOREIGN PATENT DOCUMENTS

| JP | 2005-532547 | 10/2005 |
| JP | 2015-94637 | 5/2015 |
| WO | 2016/052558 | 4/2016 |
| WO | 2016/080442 | 5/2016 |
| WO | 2017/068801 | 4/2017 |

OTHER PUBLICATIONS

Matsumoto et al. "Plasma-activated medium selectively eliminates undifferentiated human induced pluripotent stem cells" 2016, Regenerative Therapy, 5: 55-63 (Year: 2016).*
Sule-Suso et al. "Vibrational spectroscopy in stem cell characterisation: is there a niche?", 2014, Trends in Biotech, vol. 32(5): 254-262. (Year: 2014).*
Downes et al. "Optical Spectroscopy for Noninvasive Monitoring of Stem Cell Differentiation". 2010, J Biomed Biotech, vol. 2010, Article 101864, 1-10. (Year: 2010).*
Translation of the International Preliminary Report On Patentability dated Feb. 20, 2020 in International (PCT) Application No. PCT/JP2018/029770.
International Search Report (ISR) dated Oct. 30, 2018 in International (PCT) Application No. PCT/JP2018/029770.
Diletta Ami et al., "Embryonic stem cell differentiation studied by FT-IR spectroscopy", Biochimica et Biophysica Acta, 1783, pp. 98-106, 2008, cited in CA.
Oluseun Adewumi et al., "Characterization of human embryonic stem cell lines by the International Stem Cell Initiative", Nature Biotechnology, vol. 25, No. 7, pp. 803-816, Jul. 2007, cited in the specification.

* cited by examiner

Primary Examiner — Teresa E Knight
(74) Attorney, Agent, or Firm — Wenderoth, Lind & Ponack, L.L.P.

(57) ABSTRACT

The present disclosure provides a method for determining the undifferentiated state of pluripotent stem cells, comprising: irradiating a test culture medium in which pluripotent stem cells are cultured with wavelength light having a wavelength in the range of 190 nm to 2,500 nm or a partial range thereof; detecting the reflected light, transmitted light or transmitted reflected light thereof to obtain absorbance spectrum data; and analyzing the absorbance at all or part of the measurement wavelengths in the absorbance spectrum data to determine the undifferentiated state of the pluripotent stem cells.

12 Claims, 8 Drawing Sheets

METHOD FOR DETERMINING UNDIFFERENTIATED STATE OF PLURIPOTENT STEM CELL, METHOD FOR SUBCULTURING PLURIPOTENT STEM CELL, AND DEVICE FOR USE IN THE METHODS

TECHNICAL FIELD

The present disclosure relates to a method for determining the undifferentiated state of pluripotent stem cells, a method for subculturing pluripotent stem cells, and a device method for use in the methods.

BACKGROUND ART

Pluripotent stem cells are widely used in various fields such as researches on tissue differentiation, drug testing, and regenerative medicine because of their pluripotency to differentiate into any tissue. Especially, since the establishment of iPS cells, researches in this field have been remarkably developed, and various approaches for realizing regenerative medicine have been made worldwide.

Incidentally, pluripotent stem cells are easy to differentiate and may lose their pluripotency once they differentiate. Therefore, pluripotent stem cells must be cultured while their undifferentiated states are maintained. Maintaining the undifferentiated state can be said to be one of the most important elements in the culture of pluripotent stem cells.

In order to maintain the undifferentiated state, for example, an agent that inhibits differentiation is used, and pluripotent stem cells that have started to differentiate are removed. One of the biggest obstacles to large-scale preparation of pluripotent stem cells is to remove pluripotent stem cells that have started to differentiate. Insufficient removal of the cells that have started to differentiate may induce the differentiation of surrounding cells and adversely affect the entire cultured cells. However, it is difficult to determine whether pluripotent stem cells are in the undifferentiated state without relying on a skilled technician. For these reasons, large-scale preparation of pluripotent stem cells is naturally limited. Therefore, at least, the development of a method for confirming whether pluripotent stem cells are in the undifferentiated state without relying on a skilled technician's judgement and the development of a method for automatically determining pluripotent stem cells that have started to differentiate have been demanded.

As methods for confirming whether pluripotent stem cells are in the undifferentiated state, a qRT-PCR method, an immunostaining method, and a flow cytometric method have been used so far (Non-Patent Literature 1). However, the qRT-PCR method and the immunostaining method requires destruction of cells at the time of measurement. The flow cytometric method allows for nondestructive measurement, but requires suspension of cells in a single cell state, which may involve complicated operations. Therefore, noninvasive culture environment/cell quality control techniques are needed in the culture of pluripotent stem cells in regenerative medicine.

In recent years, the present inventors have reported medium analysis component analysis techniques as noninvasive culture environment/cell quality monitoring methods. Patent Literature 1 discloses a method for determining the undifferentiated state of pluripotent stem cells, comprising the step of evaluating the undifferentiated state of pluripotent stem cells based on a change over time in variation value of an extracellular metabolite contained in a culture medium in which the pluripotent stem cells are cultured, wherein the extracellular metabolite is at least one selected from the group consisting of L-glutamic acid, L-alanine and ammonia.

Patent Literature 2 discloses a method for evaluating the differentiation state of cells, comprising using stem cells which are unknown in undifferentiated state or cells which have been differentiation-induced from stem cells, as test cells, to evaluate the differentiation state of the test cells based on the amount of a predetermined indicator substance present in a culture medium of the test cells, wherein the indicator substance is at least one compound selected from the group consisting of ornithine, 2-aminoadipic acid, deoxycytidine, glutamic acid, tryptophan, asparagine, alanine, cystine, hypoxanthine, uridine, aspartic acid, arginine, 2-hydroxybutyric acid, 2-hydroxyvaleric acid, 3-hydroxyvaleric acid, urea, 4-hydroxybenzoic acid, 4-aminobenzoic acid and ribonic acid.

In the culture medium analysis techniques as described above, in the culture of pluripotent stem cells, their differentiation state can be evaluated by measuring a specific marker metabolite in a culture medium. As a technique of measuring the marker metabolite, a component separation method such as liquid chromatography (LC), gas chromatography (GC) or capillary electrophoresis (CE) and a detection technique such as a mass spectrometer (MS) are generally combined for measurement. This technique, however, may bring an increase in size of the measuring device and a low degree of freedom of data acquisition.

CITATION LIST

Patent Literatures

Patent Literature 1: WO 2016/052558
Patent Literature 2: WO 2017/068801

Non-Patent Literature

Non-Patent Literature 1: Nature Biotechnology 25, 803-816 (2007)

SUMMARY OF INVENTION

Technical Problem

On the other hand, a method is known in which regression analysis is performed on an extracellular metabolite and its spectrum information to easily and rapidly quantify the extracellular metabolite optically. However, it has been revealed, through the present disclosers' review, that, in the determination of the undifferentiated state of pluripotent stem cells, the regression model using only teacher data obtained from a culture medium that keeps pluripotency provides low quantification of the metabolite that serves as an indicator of the differentiation state, and thus cannot be used in the determination. In particular, for example, when it is necessary to determine a large amount of a culture medium of pluripotent stem cells at one time, there is a strong demand for the development of an easy and rapid examination method.

Thus, the present disclosure provides novel method and device for easily, rapidly and accurately determining the undifferentiated state of pluripotent stem cells.

Solution to Problem

As a result of intensive studies in view of the above-described problem, the present disclosure has found that, based on an analytic model created from absorbance spectrum data obtained by measuring a plurality of types of control culture media of pluripotent stem cells with specific wavelength light, the undifferentiated state of pluripotent stem cells can be determined easily, rapidly and accurately. The present disclosure is based on such findings.

A method for determining the undifferentiated state of pluripotent stem cells according to one embodiment of the present disclosure comprises the steps of:

irradiating a test culture medium in which pluripotent stem cells are cultured with wavelength light having a wavelength in the range of 190 nm to 2,500 nm or a partial range thereof, and detecting the reflected light, transmitted light or transmitted reflected light thereof to obtain absorbance spectrum data; and analyzing the absorbance at all or part of the measurement wavelengths in the absorbance spectrum data to determine the undifferentiated state of the pluripotent stem cells, based on an analytic model created in advance using a plurality of types of control culture media used to culture pluripotent stem cells, and the plurality of types of control culture media comprise:
a medium used to maintain the undifferentiated state of the pluripotent stem cells; and
at least one type of differentiation-inducing medium selected from the group consisting of a medium in which the differentiation into ectodermal cells is induced, a medium in which the differentiation into mesodermal cells is induced, and a medium in which the differentiation into endodermal cells is induced.

A method for subculturing pluripotent stem cells according to one embodiment of the present disclosure, comprises the steps of:

collecting cells necessary for subculture; and
removing cells unnecessary for culture and/or subculture,
the cells necessary for subculture are pluripotent stem cells determined to be undifferentiated cells by the above-described determination method, and
the cells unnecessary for culture and/or subculture are pluripotent stem cells determined to be cells that have started to differentiate by the above-described determination method.

A cell culture device according to one embodiment of the present disclosure comprises:

an irradiation unit that irradiates a test culture medium in which pluripotent stem cells are cultured with wavelength light having a wavelength in the range of 190 nm to 2,500 nm or a partial range thereof;
a detection unit that detects the reflected light, transmitted light or transmitted reflected light of the wavelength light applied to the sample; and
a data analysis unit that analyzes the absorbance at all the measurement wavelengths or specific measurement wavelengths in the absorbance spectrum data to determine the undifferentiated state of the pluripotent stem cells, based on an analytic model created in advance using a plurality of types of control culture media used to culture pluripotent stem cells, and
the plurality of types of control culture media comprise:
a medium used to maintain the undifferentiated state of the pluripotent stem cells; and at least one type of differentiation-inducing medium selected from the group consisting of a medium in which the differentiation into ectodermal cells is induced, a medium in which the differentiation into mesodermal cells is induced, and a medium in which the differentiation into endodermal cells is induced.

According to the present disclosure, the undifferentiated state of pluripotent stem cells can be determined easily, rapidly and accurately.

BRIEF DESCRIPTION OF DRAWINGS

FIG. 4A shows the UV spectrum of each of the culture media, and FIG. 4B is a graph obtained by secondary differential processing of the UV spectrum.

DETAILED DESCRIPTION OF THE INVENTION

Figure 1:
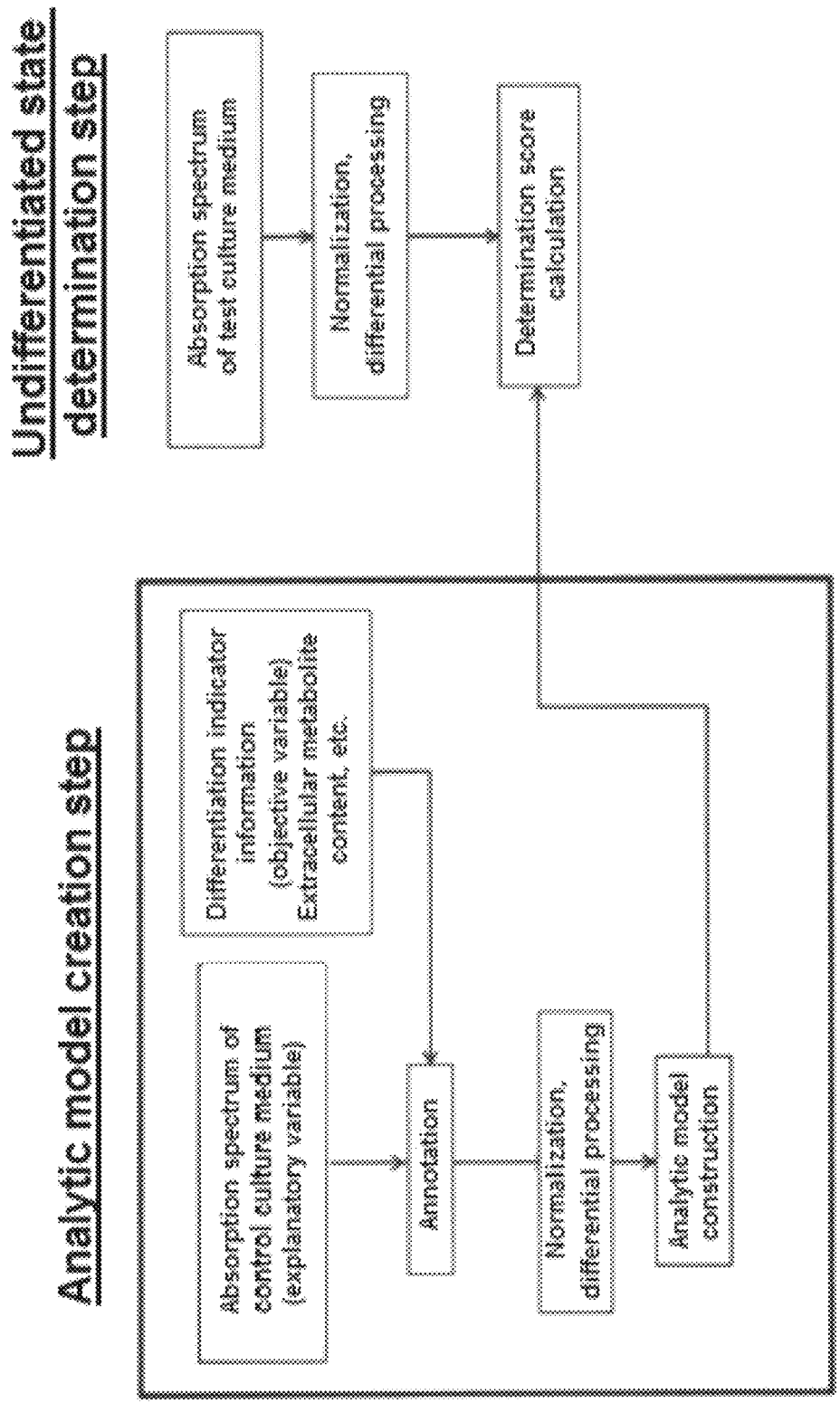
FIG. 1 is a flow chart summarizing procedures in one embodiment of the present disclosure.

In the present disclosure, the term "determination of the undifferentiated state of pluripotent stem cells" means determining whether the target pluripotent stem cells are in the undifferentiated state.

The term "pluripotent stem cells" as used in the present disclosure means cells having the ability to differentiate into cells derived from any of the three germ layers. The pluripotent stem cells used in the present disclosure are not particularly limited, but can be preferably mammalian pluripotent stem cells such as primate cells and rodent cells, more preferably human, monkey, mouse rat, guinea pig, hamster, rabbit, cat, dog, sheep, pig, cow or goat pluripotent stem cells, further preferably human pluripotent stem cells. The pluripotent stem cells used in the present disclosure include embryonic stem cells (ES cells), induced pluripotent stem cells (iPS cells or induced pluripotent stem cells), Muse cells (Multilineage-differentiating Stress Enduring Cells), embryonic tumor cells (EC cells) and embryonic germ stem cells (EG cells), and are preferably ES cells or iPS cells. Therefore, the pluripotent stem cells used in the present disclosure are preferably mammalian ES cells or iPS cells, more preferably primate or rodent ES cells or iPS cells, further preferably, human, monkey, mouse, rat, guinea pig, hamster, rabbit, cat, dog, sheep, pig, cow or goat ES cells or iPS cells, most preferably human ES cells or human iPS cells. According to the present disclosure, feeder cells may or may not be used.

The term "culture medium" (also simply referred to as "medium") used in the present disclosure means a culture medium for maintaining the undifferentiated state of pluripotent stem cells. Such a culture medium can be used without any particular limitation as long as the undifferentiated state of pluripotent stem cells can be maintained. The culture medium used in the present disclosure is not particularly limited, but can be preferably a culture medium obtained by adding a factor that contributes to maintenance of undifferentiation to a medium in which pluripotent stem cells can be cultured. As the medium in which pluripotent stem cells can be cultured, any medium can be used without any particular limitation as long as pluripotent stem cells can be cultured. Example of the medium includes Essential-8 media, TeSR-E8 media, ReproFF2 media, and mTeSR1. Examples of the factor that contributes to maintenance of undifferentiation includes bFGF, TGF-β and insulin. Note that the culture medium is replaced with a new culture medium at a predetermined time period during the culture process. The details of such replacement will be described later.

The term "differentiation-inducing medium" (also simply referred to as "medium") used in the present disclosure means a culture medium for inducing pluripotent stem cells into a differentiated state. Any differentiation-inducing medium can be used without any particular limitation as long as the differentiation of pluripotent stem cells can be induced. The differentiation-inducing medium used in the present disclosure is not particularly limited, but is preferably a culture medium (Essential-8 medium, TeSR-E8 medium, ReproFF2 medium, mTeSR1 or the like) capable of culturing pluripotent stem cells, which is added with a factor that contributes to differentiation induction, as will be described later.

In the present disclosure, pluripotent stem cells are cultured in a culture vessel to which the medium described above is added. As the culture vessel used in the present disclosure, any culture vessel can be used without any particular limitation as long as pluripotent stem cells can be cultured. For example, a dish, a multiwell plate or the like can be used.

Obtainment of Absorbance Spectrum Data

The present disclosure is characterized in that a test culture medium in which pluripotent stem cells are cultured is irradiated with wavelength light having a wavelength in the range of 190 nm to 2,500 nm or a partial range thereof, and that the absorbance at all the measurement wavelengths or specific measurement wavelengths in the obtained absorbance spectrum data is used as an indicator for determining the undifferentiated state of the pluripotent stem cells. As will be illustrated in the Example which will be described below, it has been revealed that an analytic model is created using specific control culture media, so that the undifferentiated state of pluripotent stem cells can be easily and rapidly identified using the absorbance spectrum of a test culture medium as an indicator.

From the viewpoint of obtaining a lot of information on the absorption of organic compounds in a range from the ultraviolet region to the near-infrared region, the range of the wavelength light with which the test culture medium is irradiated is in the range of 190 nm to 2,500 nm as described above, but is preferably in the range of 190 nm to 800 nm, more preferably 190 nm to 400 nm, further preferably 230 nm to 300 nm. The wavelength light range of 300 nm or less is advantageous in performing accurate quantitative analysis because of the presence of many excitation wavelengths of various functional groups of organic compounds and a relatively large change in absorption of the metabolite in the medium. Further, the wavelength light range of 190 nm or 230 nm or more is advantageous in avoiding difficulty in separating absorption of each organic matter in the medium in the absorbance measurement.

A usable light source can be a tungsten lamp or a deuterium lamp, but is not particularly limited. The light emitted from the light source can be applied to a specimen sample (culture medium) directly or via an irradiation means such as a fiber probe. As will be described later, a pre-spectroscopic method in which light is spectrally split before irradiation of a sample or a post-spectroscopic method in which light is spectrally split after irradiation may be employed, but the pre-spectroscopic method is preferred. The pre-spectroscopic method includes a method in which the light from the light source is spectrally split through a prism simultaneously at one time and a method in which the wavelength is continuously changed by changing the slit space of a diffraction grating. In the latter method, the light emitted from the light source is decomposed at predetermined wavelength intervals, whereby the sample is irradiated with continuous-wavelength light whose wavelength is changed continuously. In the Example which will be described later, light with a wavelength in the range of 230 nm to 300 nm is decomposed at a wavelength resolution of 0.1 nm, and the sample is irradiated with light whose wavelength is changed continuously in increments of 0.1 nm.

The reflected light, transmitted light, or transmitted reflected light of the light applied to the sample is detected by a detector, whereby raw absorbance spectrum data is obtained. The raw absorbance spectrum data may be used as it is for examination/determination using an analytical model, but it is preferable to perform data conversion processing such as decomposition of peaks in the obtained spectrum into elemental peaks using a spectroscopic or multivariate analysis technique and to perform the examination/determination using the analytical model using the converted absorbance spectrum data. The data conversion processing is not particularly limited. Examples of the spectroscopic technique include secondary differential processing and Fourier transform, and examples of the multivariate analysis technique include wavelet conversion and a neural network method. However, secondary differential processing is preferably performed from the viewpoint of easy noise removal and the like.

Data Analysis Method (Creation of Analytic Model)

In the present disclosure, the absorbance at all or part of the measurement wavelengths in the absorbance spectrum data obtained in the above-described manner is analyzed using an analytic model to determine the undifferentiated state of pluripotent stem cells.

The analytic model of the present disclosure is created using a plurality of types of control culture media used to culture pluripotent stem cells, and the control culture media are formed to include a medium used to maintain the undifferentiated state of the pluripotent stem cells and at least one type of differentiation-inducing medium selected from the group consisting of a medium in which the differentiation into ectodermal cells is induced, a medium in which the differentiation into mesodermal cells is induced, and a medium in which the differentiation into endodermal cells is induced. Using a plurality of types of differentiation-inducing media which are different in differentiation-inducing direction to create an analytic model using their absorbance spectrum data and other physical property values is especially advantageous in obtaining an analytic model to accurately determine the undifferentiated state of pluripotent stem cells.

The at least one type of differentiation-inducing medium used to create the analytic model together with the medium used to maintain the undifferentiated state of pluripotent stem cells preferably includes two or more types of differentiation-inducing media selected from the group consisting of a medium in which the differentiation into ectodermal cells is induced, a medium in which the differentiation into mesodermal cells is induced, and a medium in which the differentiation into endodermal cells is induced, more preferably three types of differentiation-inducing media consisting of a medium in which the differentiation into ectodermal cells is induced, a medium in which the differentiation into mesodermal cells is induced, and a medium in which the differentiation into endodermal cells is induced. Using the differentiation-inducing media in which the differentiation into the respective germ layers is induced together with the culture medium in which undifferentiated pluripotent stem cells are cultured to create the analytic model is advantageous in remarkably improving the accuracy of determining the undifferentiated state of pluripotent stem cells.

In addition, as the differentiation-inducing media in which the differentiation into ectodermal cells, mesodermal cells and endodermal cells, respectively, is induced, culture media added with a factor that contributes to induction of differentiation into the respective germ layer cells are suitably used in the analytic model of the present disclosure. Those skilled in the art can appropriately set the types and amounts of the above-described factors to be added depending on the accuracy of the determination using the analytic model.

Examples of the factor to be added contained in the medium in which the differentiation into ectodermal cells is induced include SB431542, Noggin, Dorsomorphin, CKI-7 and VEGF, and combinations thereof.

Examples of the factor to be added contained in the medium in which the differentiation into mesodermal cells is induced include BMP4, retinoic acid and SCF, and combinations thereof.

Examples of the factor to be added contained in the medium in which the differentiation into endodermal cells is induced include Activin-A, Wnt-3a, BMP4, CHIR99021 and Wortmanninm, and combinations thereof.

In the present disclosure, it is preferable to utilize used culture media which have been replaced by medium replacement as both the test culture medium and the control culture media. By repeatedly utilizing the used culture media which have been replaced by medium replacement to create the analytic model, the state change, over time, of pluripotent stem cells can be advantageously monitored.

During the culture process of the pluripotent stem cells, the time period of the medium replacement can be appropriately determined by those skilled in the art, and can be for example 12 to 72 hours, preferably 24 to 48 hours.

The phrase "during the culture process" means the steps in which pluripotent stem cells are seeded in a culture vessel to which the culture medium is added, cultured, and then passaged. The pluripotent stem cells can be seeded at a density such that the medium replacement is performed 1 to 5 times, preferably 2 to 4 times, more preferably 3 to 4 times during the culture process.

Other culture conditions can be appropriately determined by those skilled in the art according to the state of the pluripotent stem cells to be used.

In the method for determining the undifferentiated state of pluripotent stem cells of the present disclosure, an analytic model must be created in advance based on information on the medium used to maintain the undifferentiation or the media in which the differentiation into the respective germ layer cells is induced. Of course, this analytic model may be created at the time of spectrum measurement, and such an aspect falls within the scope of the "created in advance" in the present disclosure.

The analytic model can be created by multivariate analysis. For example, when determining the undifferentiated state of pluripotent stem cells, a data matrix that stores the absorption spectrum at all the wavelengths obtained by the spectrum measurement of each target culture medium is decomposed into score and loading by singular value decomposition. Then, the principal component that summarizes the variation in undifferentiated state in a sample is extracted (principal component analysis). This allows an independent component with low collinearity (=high correlation between explanatory variables) to be used in multiple linear regression analysis. Then, multiple linear regression analysis using an explanatory variable which is the absorption spectrum data (score) and an objective variable which is the physical property value of each target culture medium as an indicator of the undifferentiated state of pluripotent stem cells, is applied. This makes it possible to create the analytic model to estimate the undifferentiated state of the pluripotent stem cells from the absorption spectrum at all the measurement wavelengths or specific measurement wavelengths. The series of operations (multivariate analyses) have been established as a Principal Component Regression (PCR) method or a Partial Least Squares (PLS) regression method (reference document: Multivariate Analysis for Chemists—Introduction to Chemometrics," Yukihiro Ozaki, Akifumi Uda & Toshio Akai; published by Kodansha Ltd., 2002). Examples of the regression analysis method include a classical least squares (CLS) method, in addition to these methods. According to one aspect of the present disclosure, the analytic model is created by regression analysis that is a PLS method.

In the creation of the analytic model of the present disclosure as described above, the characteristic values of the control culture media are appropriately set as the explanatory variable and the objective variable by those skilled in the art, from the viewpoint of appropriate determination of the undifferentiated state of pluripotent stem cells. Examples of the explanatory variable include the absorbance spectrum data for wavelength light having a wavelength in the range of 190 nm to 2,500 nm or a partial range thereof. Preferably, the explanatory variable is similar to that used for the light applied to the test culture medium as described above.

From the viewpoint of appropriate determination of the undifferentiated state of pluripotent stem cells, the objective variable is preferably the content of an extracellular metabolite that can be associated with the differentiation state of pluripotent stem cells. Examples of the extracellular metabolite include L-glutamic acid, L-alanine, ammonia, ornithine, 2-aminoadipic acid, deoxycytidine, glutamic acid, tryptophan, aspartic acid, alanine, cystine, hypoxanthine, uridine, 2-hydroxybutyric acid, 2-hydroxyvaleric acid, 3-hydroxyvaleric acid, 2-hydroxyisovaleric acid, 3-hydroxyisovaleric acid, urea, 4-hydroxybenzoic acid, 4-aminobenzoic acid and ribonic acid, and combinations thereof. The content of the extracellular metabolite is an amount obtained by subtracting the amount of the metabolite consumed in pluripotent stem cells from the amount of the metabolite secreted from the cells into the culture medium during the culture of the cells.

The means for measuring the extracellular metabolite in the culture medium can be selected, without any particular limitation, depending on the type and properties of the extracellular metabolite. Examples of the measuring means include an enzyme electrode method, a colorimetric method, gas chromatography, gas chromatography mass spectrometry, liquid chromatography, high performance liquid chromatography mass spectrometry, and capillary electrophoresis mass spectrometry. Preferably, a commercially available analyzer such as BioFlow (trademark) STAT Biosensor BM-7M (manufactured by Oji Scientific Instruments) using the enzyme electrode method can be used.

While the above method is used to create a quantitative analytic model, a multivariate analysis such as Principal Component Analysis (PCA) for class discrimination, a SIMCA (soft independent modeling of class analogy) method or a KNN (k nearest neighbors) method may be used to create a qualitative analytic model. In the SIMCA method, principal component analysis is performed on each of a plurality of groups (classes) to create a principal component model of each class. Then, an unknown sample is compared with the principal component model of each class, and assigned to the principal component model of the class which the unknown sample matches best. Class discriminant analysis such as the SIMCA method can be said to be a method of classifying absorption spectra or regression vectors into respective classes by pattern recognition.

The creation of the analytic model using the above multivariate analysis can be performed using self-made software or commercially available multivariate analysis software. In addition, rapid analysis can be realized by creating software specialized for the purpose of use as a program for determining the undifferentiated state of pluripotent stem cells.

The determination of the undifferentiated state of pluripotent stem cells involves analyzing the degree of variation in undifferentiated state as compared with the analytic model obtained by the above-described measurement. It is possible to determine that the cells are in the undifferentiated state when the degree of variation falls within a reference range, and to determine that the cells are not in the undifferentiated state when the degree of variation falls outside the reference range.

For example, the determination of the undifferentiated state of pluripotent stem cells involves comparing the absorbance in the test culture medium with a threshold value preset by the analytic model. It is possible to determine that the cells are in a differentiated state when the absorbance is higher than the threshold value.

The analytic model assembled using such multivariate analysis software is stored as a file, and this file is called up at the time of measuring an unknown sample to perform quantitative or qualitative examination/diagnosis on the unknown sample using the analytic model. This enables easy and rapid noninvasive determination of the undifferentiated state of pluripotent stem cells. As the analytic model, a plurality of analytic models such as a quantitative model and a qualitative model are stored as files, and are preferably each updated as appropriate.

According to the present disclosure, the determination of the undifferentiated state of pluripotent stem cells based on the analysis results of the culture medium in which pluripotent stem cells are cultured can be automated, in the entire process, by a computer or the like. Accordingly, there is provided a program for causing a computer to execute the method of the present disclosure. Specifically, according to the present disclosure, there is provided a program for causing a computer to execute the steps of obtaining the analysis results of the culture medium in which pluripotent stem cells are cultured and automatically determining the undifferentiated state of the pluripotent stem cells based on the analysis result. According to the present disclosure, there is also provided a computer-readable recording medium in which the program of the present disclosure is recorded. According to the present disclosure, there is further provided an automatic determination system for evaluating the undifferentiated state of pluripotent stem cells, including a computer in which the program of the present disclosure is recorded in its internal recording device or the computer of the present disclosure.

The program of the present disclosure may be recorded in a recording medium such as a flexible disk or a CD-ROM and read and executed by the computer. The recording medium is not limited to a removable medium such as a magnetic disk or an optical disk, but may be a fixed recording medium such as a hard disk device or a memory. Further, the program of the present disclosure may be distributed via a communication line (including wireless communication) such as the Internet. Further, in a state of being encrypted, modulated or compressed, the program may be distributed via a wired or wireless line such as the Internet or in a state of stored in a recording medium.

The method for determining the undifferentiated state of pluripotent stem cells of the present disclosure, as described above, can be used in a cell culture method. As one aspect of the present disclosure, there is provided a cell culture method for culturing pluripotent stem cells in the undifferentiated state, comprising the steps of:

(a) performing incubation on a culture vessel containing undifferentiated pluripotent stem cells and a culture medium;

(b) performing medium replacement on the culture vessel after completion of step (a);

(c) irradiating the incubated medium collected in step (b) with wavelength light having a wavelength in the range of 190 nm to 2,500 nm or a partial range thereof, and detecting the reflected light, transmitted light, or transmitted reflected light thereof to obtain absorbance spectrum data; and (d) based on an analytic model created in advance using a plurality of types of control culture media used to culture pluripotent stem cells, analyzing the absorbance at all or part of the measurement wavelengths in the absorbance spectrum data to determine the undifferentiated state of the pluripotent stem cells, wherein the plurality of types of control culture media include: a medium used to maintain the undifferentiated state of the pluripotent stem cells; and at least one type of differentiation-inducing medium selected from the group consisting of a medium in which the differentiation into ectodermal cells is induced, a medium in which the differentiation into mesodermal cells is induced, and a medium in which the differentiation into endodermal cells is induced.

The present disclosure makes it possible to determine the undifferentiated state of pluripotent stem cells without destroying the cells. It is possible to continue the culture when it is determined by the method that the pluripotent stem cells are undifferentiated, and, on the other hand, to remove the cells when it is determined that the pluripotent stem cells have started to differentiate. Therefore, the determination method according to the present disclosure can be applied to a method for subculturing pluripotent stem cells.

In the subculture method of the present disclosure, the cells determined to have started to differentiate by the determination method of the present disclosure can be removed as cells unnecessary for culture and/or subculture. The unnecessary cells can be removed during culture, or can also be removed at the time of subculture. The unnecessary cells may be removed position-specifically in the culture vessel via observation by optical microscope or the like, in view of the characteristic of the present disclosure that culture medium analysis is performed. Position-specific exfoliation/removal of the cells in the culture vessel can be carried out, for example, based on the description of WO2015/058841.

FIG. 1 shows a summary of the analytic model creation step and the undifferentiated state determination step using the analytic model, as described above. In the analytic model creation step, for example, the culture medium in which pluripotent stem cells are cultured is irradiated with wavelength light having a wavelength in the range of 190 nm to 2,500 nm or a partial range thereof. Subsequently, the obtained absorbance spectrum data is annotated with differentiation indicator information (for example, content of the extracellular metabolite which serves as a cell differentiation indicator), and subjected to preprocessing such as normalization and differential processing. Then, multivariate analysis is performed using the absorbance spectrum data as an explanatory variable and the differentiation indicator information as an objective variable to create an analytic model. The undifferentiated state is scored in advance using the thus-created analytic model, and the absorption spectrum of an unknown sample (test culture medium) is measured. Through preprocessing such as normalization and differential processing, the determination score of the undifferentiated state of the unknown sample is calculated based on the analytic model, thereby making it possible to determine the undifferentiated state of the pluripotent stem cells. If an analytic model evaluated higher than the previously-created analytic model can be obtained, the model can be appropriately reconstructed, for example, by update.

Figure 2:
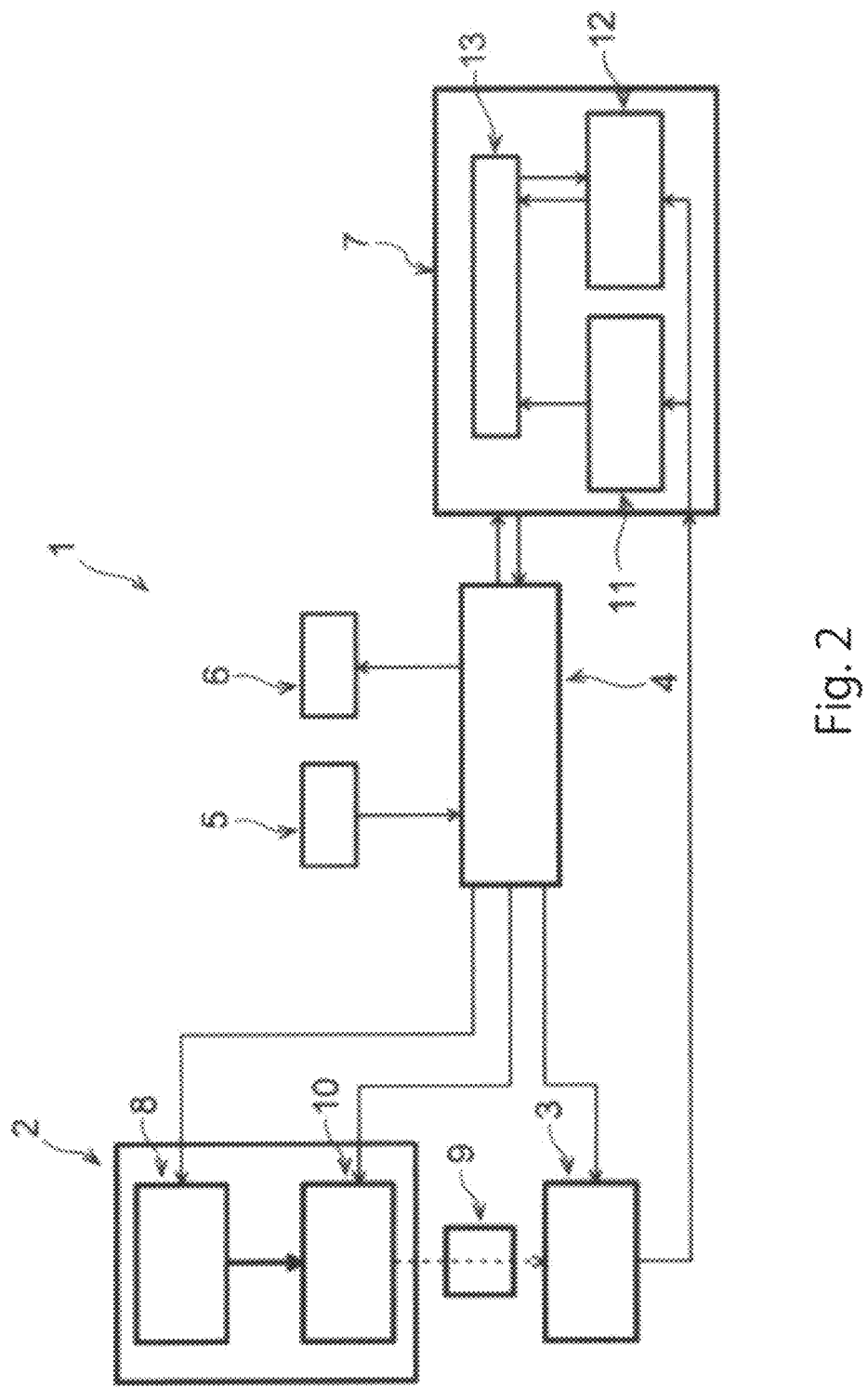
FIG. 2 is a schematic diagram showing the structure of a cell culture device that determines the undifferentiated state of pluripotent stem cells according to one embodiment of the present disclosure.

Next, a cell culture device for determining the undifferentiated state of pluripotent stem cells according to one embodiment of the present disclosure will be described with reference to FIG. 2. FIG. 2 is a schematic diagram showing the structure of the device according to one embodiment of the present disclosure. In FIG. 2, the connection of wiring is shown by a solid line, and the wavelength light applied to the culture medium is shown by a broken line.

A device 1 according to the present embodiment is a device for determining the undifferentiated state of pluripotent stem cells. The device 1 cultures pluripotent stem cells while determining whether pluripotent stem cells are in the undifferentiated state through cell state determination based on cell morphology observation and cell state determination based on component analysis of the medium used to culture the cells (if necessary, while removing the cells having started to differentiate, which are identified by the determination), so that the pluripotent stem cells can be cultured in the undifferentiated state.

As shown in FIG. 2, the device 1 can be formed to include an irradiation unit 2, a detection unit 3, a control unit 4, an input unit 5, an output unit 6, and a data analysis unit 7. Hereinafter, each element will be described.

The irradiation unit 2 has the function of guiding wavelength light (having a wavelength in the whole or partial range of 190 nm to 2,500 nm) from a light source 8 such as a UV lamp or an LED to a sample 9 to be measured. The irradiation unit 2 may be provided with a probe. As the probe, for example, a fiber probe such as an optical fiber can be selected, and light may be projected to a target to be measured (sample) via the fiber.

Note that the light emitted from the light source 8 may be directly applied to the sample to be measured. In this case, no probe is necessary, and the light source functions as the irradiation unit.

When the analytic model is created as described above, the wavelength light necessary for determining the undifferentiated state using the analytic model is decided. The present device is formed to irradiate the sample with the thus-decided wavelength light in one or more wavelength regions.

The present device 1 further includes a spectroscope 10 in the irradiation unit 2. As shown in FIG. 2, the pre-spectroscopy method in which light is spectrally split by a spectroscope before irradiation of a culture medium as shown in FIG. 2 includes a method in which the light from the light source 8 is spectrally split through a prism simultaneously at one time and a method in which the wavelength is continuously changed by changing the slit space of a diffraction grating. In the latter method, the light emitted from the light source is decomposed at predetermined wavelength intervals, whereby the culture medium is irradiated with continuous-wavelength light whose wavelength is changed continuously. For example, it is possible to decompose light with a wavelength in the range of 230 to 300 nm at a wavelength resolution of 0.1 nm, and to irradiate the culture medium with light whose wavelength is changed continuously in increments of 0.1 nm. In FIG. 2, the pre-spectroscopic method is employed, but a post-spectroscopic method in which light is spectrally split after irradiation of the culture medium may be employed, and such an aspect also falls within the present disclosure. The above-described spectroscope 10 can be formed by a known means.

In addition, the present device 1 further includes a detection unit 3 that detects the reflected light, transmitted light, or transmitted reflected light of the wavelength light applied to the culture medium from the irradiation unit 2. There are three types of detection methods, including reflected light detection, transmitted light detection, and transmitted reflected light detection. In the reflected light detection and the transmitted light detection, a detector detects the reflected light and the transmitted light, respectively, from the object to be measured. In the transmitted reflected light detection, the light which enters the object to be measured, is refracted and reflected in the object, and emitted again out of the object is detected. The detection unit 3 of the present device may employ any of the detection methods, i.e., the reflected light detection, the transmitted light detection, and the transmitted reflected light detection.

In the detection unit 3, for example, a CCD (Charge Coupled Device), which is a semiconductor element, can be used as the detector that detects the reflected light, transmitted light, or transmitted reflected light of the wavelength light applied to the culture medium. However, the detector is, of course, not limited to this, and other light receiving elements may be used.

Although not shown, the detection unit 3 may be formed integrally with or separately from a culture vessel placement part for placing a vessel containing the culture medium in which pluripotent stem cells are cultured, an incubation part for incubating the culture vessel, and a medium replacement part for medium replacement. Those skilled in the art can place the culture vessel placement part, the incubation part, and the medium replacement part based on the known technique described in Patent Literature 2 or the like.

The absorbance for each wavelength, that is, absorbance spectrum data, is obtained from the detection unit. The data analysis unit creates an analytic model based on the absorbance spectrum data in accordance with an instruction signal from the control unit 4 which will be described later, and further determines the differentiation state of the undifferentiated cells cultured in the test culture medium uses the created analytic model.

The control unit 4 can control the operations of the irradiation unit 2 (the light source 8 and the spectroscope 10) and the detection unit 3 to control the timing of measurement (light reception), the intensity of the light source, and the like. The control unit 4 is composed of, for example, a computer including a CPU, a RAM, a ROM, and the like, and performs various types of processing based on various types of data, various programs, and the like stored in the cell culture device 1.

The input unit 5 is composed of, for example, a keyboard or a pointing device such as a mouse operated by an operator, and inputs various operation signals such as an instruction from the operator (for example, an instruction to start processing or an instruction to display the results of processing) or input of data required for each processing. The input data is stored by the control unit 4.

The output unit 6 is composed of a display or the like, and outputs the results obtained or analyzed by various means (for example, analysis results of the differentiation state of the undifferentiated cells). In particular, the output unit 6 displays the analysis results in the data analysis unit 7. Specifically, the differentiation state obtained as results of analysis using the analytic model, for example, is displayed. In the case of the qualitative model, based on the class discrimination results, the indications "differentiated", "highly likely to differentiate," "less likely to differentiate," "highly differentiated", "less differentiated," "undifferentiated state" and the like are displayed. When the present device is downsized, a flat display such as a liquid crystal display is preferably used as the output unit 6.

The data analysis unit 7 includes, for example, a main storage unit 11, an auxiliary storage unit 12 and an arithmetic processing unit 13. In particular, the main storage unit 11 is composed of a RAM (Random Access Memory) or the like, and temporarily stores a measurement program and data. More specifically, the main storage unit 11 records the intensity of light received by the detection unit 3. The auxiliary storage unit 12 is a hard disk drive (HDD) or the like, and, for example, can record data similar to that recorded in the main storage unit 11, and can further record the analytic model created by the arithmetic processing unit 13, determination results, and the like. The arithmetic processing unit 13 is a CPU (Central Processing Unit) or the like, and, based on the data and programs supplied from the main storage unit 11 and the auxiliary storage unit 12, performs arithmetic processing for creation of the analytic model, determination of the undifferentiated state of pluripotent stem cells, etc. A plurality of analytic models such as a quantitative model and a qualitative model may be prepared, and different models may be used depending on whether to perform quantitative or qualitative evaluation.

As described above, the present device 1 can be used to determine the undifferentiated state of pluripotent stem cells. Here, the determination of the undifferentiated state of pluripotent stem cells is not limited to mere determination as to whether the cells are in the undifferentiated state, but means various determinations concerning the differentiation state of the pluripotent stem cells, such as quantitative evaluation of the degree of differentiation (the degree of the undifferentiated state) and the degree of progress of differentiation, and evaluation and determination of a differentiation risk.

According to one embodiment of the present disclosure, the following (1) to (21) are provided.

(1) A method for determining the undifferentiated state of pluripotent stem cells, comprising:
  irradiating a test culture medium in which pluripotent stem cells are cultured with wavelength light having a wavelength in the range of 190 nm to 2,500 nm or a partial range thereof, and detecting the reflected light, transmitted light or transmitted reflected light thereof to obtain absorbance spectrum data; and
  analyzing the absorbance at all or part of the measurement wavelengths in the absorbance spectrum data to determine the undifferentiated state of the pluripotent stem cells, based on an analytic model created in advance using a plurality of types of control culture media used to culture pluripotent stem cells,
  wherein the plurality of types of control culture media comprise: a medium used to maintain the undifferentiated state of the pluripotent stem cells; and at least one type of differentiation-inducing medium selected from the group consisting of a medium in which the differentiation into ectodermal cells is induced, a medium in which the differentiation into mesodermal cells is induced, and a medium in which the differentiation into endodermal cells is induced.

(2) The determination method according to (1), wherein the plurality of types of differentiation-inducing media include the medium in which the differentiation into ectodermal cells is induced, the medium in which the differentiation into mesodermal cells is induced and the medium in which the differentiation into endodermal cells is induced.

(3) The method according to (1) or (2), wherein the medium in which the differentiation into ectodermal cells is induced comprises at least one differentiation inducer selected from the group consisting of: SB431542, Noggin, Dorsomorphin, CKI-7 and VEGF.

(4) The method according to any one of (1) to (3), wherein the medium in which the differentiation into mesodermal cells is induced comprises at least one differentiation inducer selected from the group consisting of BMP4, retinoic acid and SCF.

(5) The method according to any one of (1) to (4), wherein the medium in which the differentiation into endodermal cells is induced comprises at least one differentiation inducer selected from the group consisting of Activin-A, Wnt-3a, BMP4, CHIR99021 and Wortmannin.

(6) The determination method according to any one of (1) to (5), which is a method for noninvasively determining the undifferentiated state of pluripotent stem cells.

(7) The determination method according to any one of (1) to (6), wherein the analytic model is created using, as an explanatory variable, the absorbance spectrum data of the plurality of types of control culture media for the wavelength light having a wavelength in the range of 190 nm to 2,500 nm or a partial range thereof.

(8) The method according to any one of (1) to (7), wherein the analytic model is created using, as objective variables, the contents of an extracellular metabolite in the plurality of types of control culture media.

(9) The method according to any one of (1) to (8), wherein the extracellular metabolite is at least one selected from the group consisting of L-glutamic acid, L-alanine, ammonia, ornithine, 2-aminoadipic acid, deoxycytidine, glutamic acid, tryptophan, aspartic acid, alanine, cystine, hypoxanthine, uridine, 2-hydroxybutyric acid, 2-hydroxyvaleric acid, 3-hydroxyvaleric acid, 2-hydroxyisovaleric acid, 3-hydroxyisovaleric acid, urea, 4-hydroxybenzoic acid, 4-aminobenzoic acid, and ribonic acid.

(10) The method according to any one of (1) to (9), wherein the analytic model is created by regression analysis that is a PLS method.

(11) The method according to any one of (1) to (10), wherein the test culture medium and the control culture media are used culture media which have been replaced by medium replacement.

(12) The method according to (11), wherein the time period of the medium replacement is 24 to 48 hours.

(13) A program for causing a computer to execute the method according to any one of (1) to (12).

(14) A computer-readable recording medium in which the program according to (13) is recorded.

(15) A computer-readable recording medium in which the program according to (13) is recorded in its internal storage device.

(16) A system for automatically determining the undifferentiated state of pluripotent stem cells, comprising the computer according to (15).

(17) A method for subculturing pluripotent stem cells, comprising the steps of:
collecting cells necessary for subculture; and
removing cells unnecessary for culture and/or subculture,
wherein the cells necessary for subculture are pluripotent stem cells determined to be undifferentiated cells by the determination method according to any one of (1) to (12), and
wherein the cells unnecessary for culture and/or subculture are pluripotent stem cells evaluated to be cells that have started to differentiate by the determination method according to any one of (1) to (12).

(18) A cell culturing method for culturing the undifferentiated state of pluripotent stem cells, comprising the steps of:
(a) performing incubation on a culture vessel containing undifferentiated pluripotent stem cells and a culture medium;
(b) performing medium replacement on the culture vessel after completion of step (a);
(c) irradiating the incubated medium collected in step (b) with wavelength light having a wavelength in the range of 190 nm to 2,500 nm or a partial range thereof, and detecting the reflected light, transmitted light, or transmitted reflected light thereof to obtain absorbance spectrum data; and
(d) based on an analytic model created in advance using a plurality of types of control culture media used to culture pluripotent stem cells, analyzing the absorbance at all the measurement wavelengths or specific measurement wavelengths in the absorbance spectrum data to determine whether the pluripotent stem cells is in the undifferentiated state,
wherein the plurality of types of control culture media include: a medium used to maintain the undifferentiated state of the pluripotent stem cells; and at least one type of differentiation-inducing medium selected from the group consisting of a medium in which the differentiation into ectodermal cells is induced, a medium in which the differentiation into mesodermal cells is induced, and a medium in which the differentiation into endodermal cells is induced.

(19) A device for determining the undifferentiated state of pluripotent stem cells, comprising:
an irradiation unit that irradiates a test culture medium in which pluripotent stem cells are cultured with wavelength light having a wavelength in the range of 190 nm to 2,500 nm or a partial range thereof;
a detection unit that detects the reflected light, transmitted light or transmitted reflected light of the light applied to the sample; and
a data analysis unit that, based on an analytic model created in advance using a plurality of types of control culture media used to culture pluripotent stem cells, analyzes the absorbance at all the measurement wavelengths or specific measurement wavelengths in the absorbance spectrum data to determine the undifferentiated state of the pluripotent stem cells, and
wherein the plurality of types of control culture media include: a medium used to maintain the undifferentiated state of the pluripotent stem cells; and at least one type of differentiation-inducing medium selected from the group consisting of a medium in which the differentiation into ectodermal cells is induced, a medium in which the differentiation into mesodermal cells is induced, and a medium in which the differentiation into endodermal cells is induced.

(20) The device according to (19), further comprising a spectral split unit that spectrally splits the light before or after the irradiation.

(21) The device according to (19) or (20), wherein the data analysis unit creates the analytic model using the plurality of types of control culture media used to culture pluripotent stem cells.

EXAMPLE

Hereinafter, the present disclosure will be described in detail by way of a specific example, but it should not be understood that the present disclosure is limited by specific aspects of the example. It should be understood that the present disclosure includes all modifications and alterations of the invention disclosed in the example.

Example 1: Review on Relationship Between Undifferentiated State of Pluripotent Stem Cells and Components of Culture Medium One Example of evaluation for the differentiation state of cells by the method according to the present disclosure will be described below.

Figure 3:
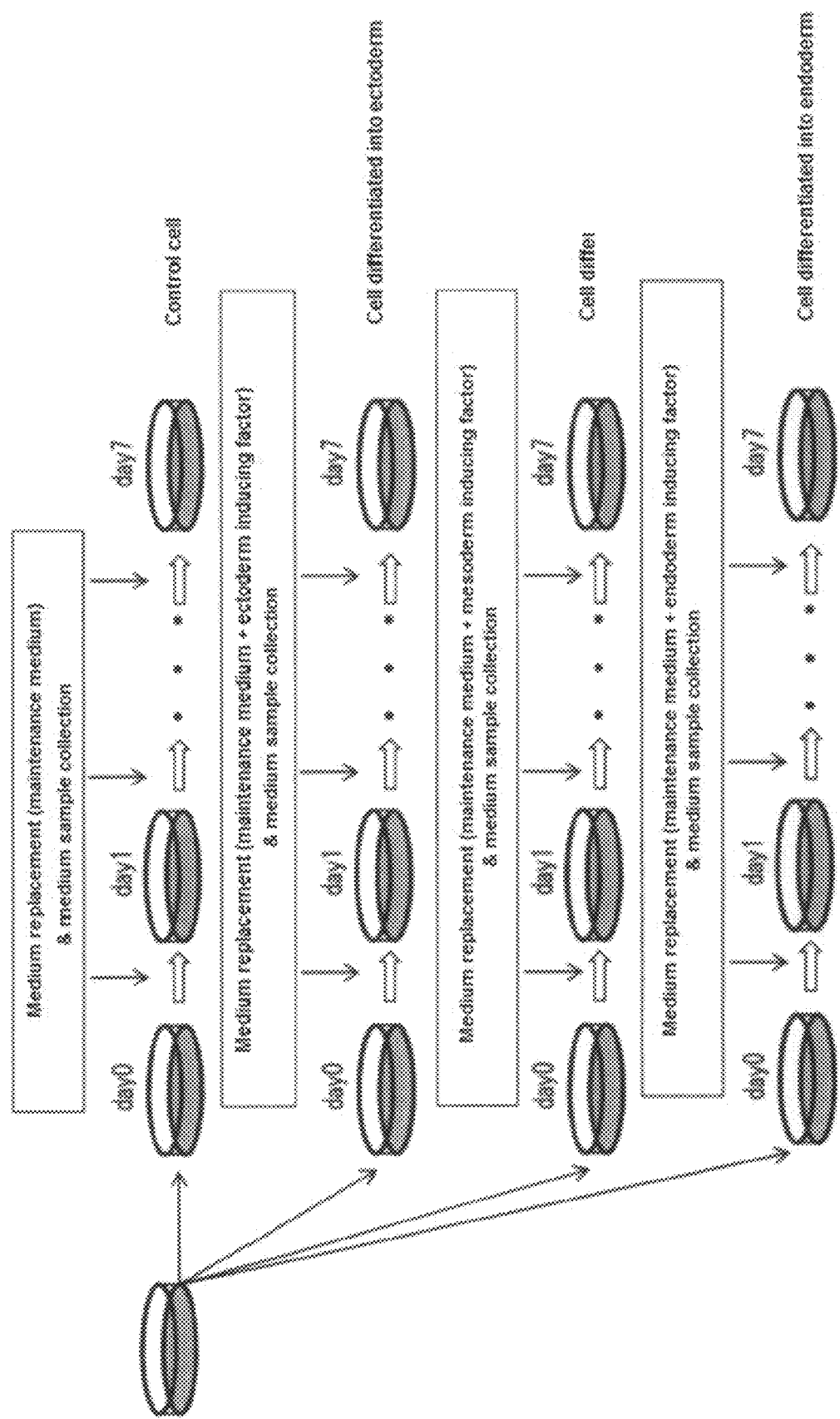
FIG. 3 is a schematic diagram illustrating a method of collecting culture media used in creating an analytic model in an Example of one embodiment of the present disclosure.

FIG. 3 is a schematic diagram showing procedures to be carried out for collecting a culture medium sample for creating an evaluation model for the cell differentiation state according to this Example.

In this Example, the human iPS cell strain PFX #9 was used. A human iPS cell strain to which a differentiation-inducing stimulus was applied was used as a test cell, and a human iPS cell strain to which no differentiation-inducing stimulus was applied (i.e., a cell whose undifferentiated state was maintained) was used as a control cell. Hereinafter, the procedures from the cell culture to the analysis of culture medium samples (culture supernatant) in this Example will be described.

The control cells and their culture medium samples were prepared according to the following procedures.

[Culture of Control Cell and Collection of Culture Supernatant]

The above PFX #9 strain was subcultured in three culture dishes (diameter: 60 mm) coated with Vitronectin-N(Life Technologies) (FIG. 1A shows only one culture dish for simplicity). TeSR-E8 (STEMCELL Technologies) was used as a maintenance medium, and medium replacement was performed every day. The culture was continued until day 7, with the day of cell subculture (passage) defined as day 0. The culture medium collected from the culture dishes at the time of medium replacement on each day was used as a sample for mass analysis.

Ectodermal cells, mesodermal cells and endodermal cells induced from the control cells and culture medium samples thereof were obtained according to the following procedures.

[Culture of Cell Differentiated into Ectoderm and Collection of Culture Medium]

The above PFX #9 strain was subcultured in three culture dishes (diameter: 60 mm) coated with Vitronectin-N(FIG. 3 shows only one culture dish for simplicity). TeSR-E8 was used as a medium. The medium was replaced every day, and the culture was continued until confluent. With the day of passage defined as day 0, on day 1 and later, the medium was replaced with a medium added with ectodermal differentiation-inducing factors (SB431542 (4-[4-(1,3-benzodioxol-5-yl)-5-(2-pyridinyl)-1H-imidazol-2-yl]benzamide (Wako Pure Chemical Industries, Ltd.) and Noggin (PeproTech)) to final concentrations of 10 μM and 500 ng/mL, respectively, to induce an ectodermal differentiation-inducing stimulus. The culture was continued until day 7, with the day of cell subculture (passage) defined as day 0. The culture medium collected from the culture dishes at the time of medium replacement on each day was used as a sample for mass analysis.

[Culture of Cell Differentiated into Mesoderm and Collection of Culture Medium]

The above PFX #9 strain was subcultured in three culture dishes (diameter: 60 mm) coated with Vitronectin-N(FIG. 3 shows only one culture dish for simplicity). TeSR-E8 was used as a medium. The medium was replaced every day, and the culture was continued until confluent. With the day of passage defined as day 0, on day 1 and later, the medium was replaced with a medium added with a mesodermal differentiation-inducing factor (BMP-4) to a final concentration of 40 ng/mL to induce a mesodermal differentiation-inducing stimulus. The culture was continued until day 7, with the day of cell subculture (passage) defined as day 0. The culture medium collected from the culture dishes at the time of medium replacement on each day was used as a sample for mass analysis.

[Culture of Cell Differentiated into Endoderm and Collection of Culture Medium]

The above PFX #9 strain was subcultured in three culture dishes (diameter: 60 mm) coated with Vitronectin-N(FIG. 3 shows only one culture dish for simplicity). TeSR-E8 was used as a medium. The medium was replaced every day, and the culture was continued until confluent. With the day of passage defined as day 0, on day 1, the medium was replaced with a medium added with endodermal differentiation-inducing factors (Activin-A, PeproTech), Wnt3a (Wingless-type MMTV integration site, family, member 3A, PeproTech) and BMP-4 (Bone Morphogenetic Protein-4, PeproTech)) to final concentrations of 100 ng/mL, 40 ng/mL and 0.5 ng/mL, respectively. On day 2 and later, the medium was replaced with a medium added with Activin-A and BMP-4 to final concentrations of 100 ng/mL and 0.5 ng/mL, respectively, to induce an endodermal differentiation-inducing stimulus. The culture was continued until day 7, with the day of cell subculture (passage) defined as day 0. The culture medium collected from the culture dishes at the time of medium replacement on each day was used as a sample for analysis.

[UV Spectrum Measurement of Culture Medium]

Figure 4A:
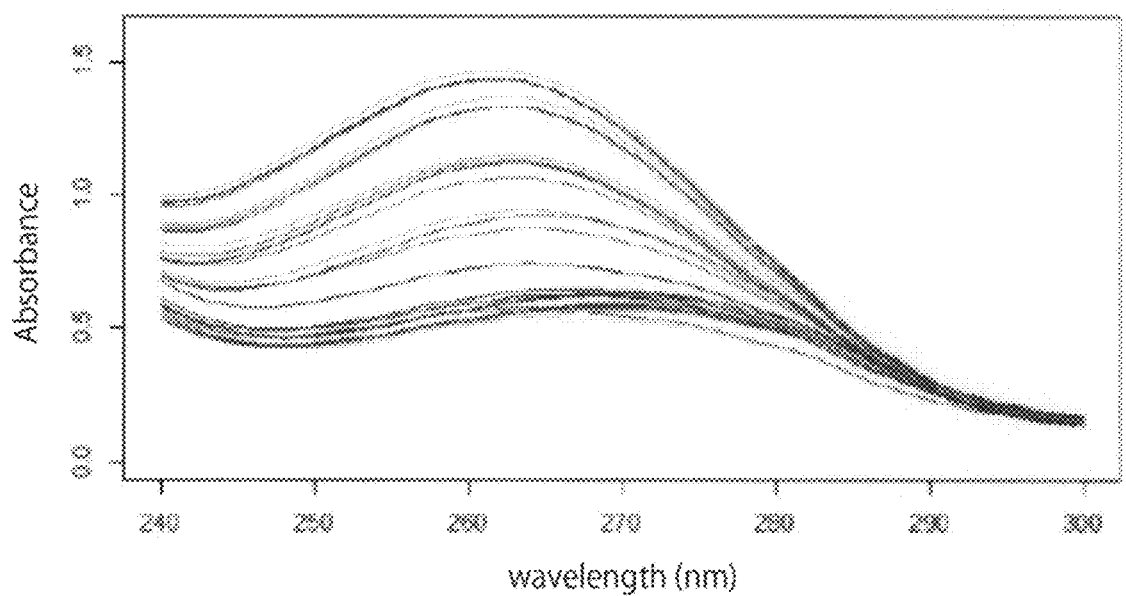
FIG. 4A and FIG. 4B are graphs showing the results of measurement of a UV spectrum at wavelengths in the range of 240 nm to 300 nm for each of the culture media obtained in the Example of one embodiment of the present disclosure.
Figure 4B:
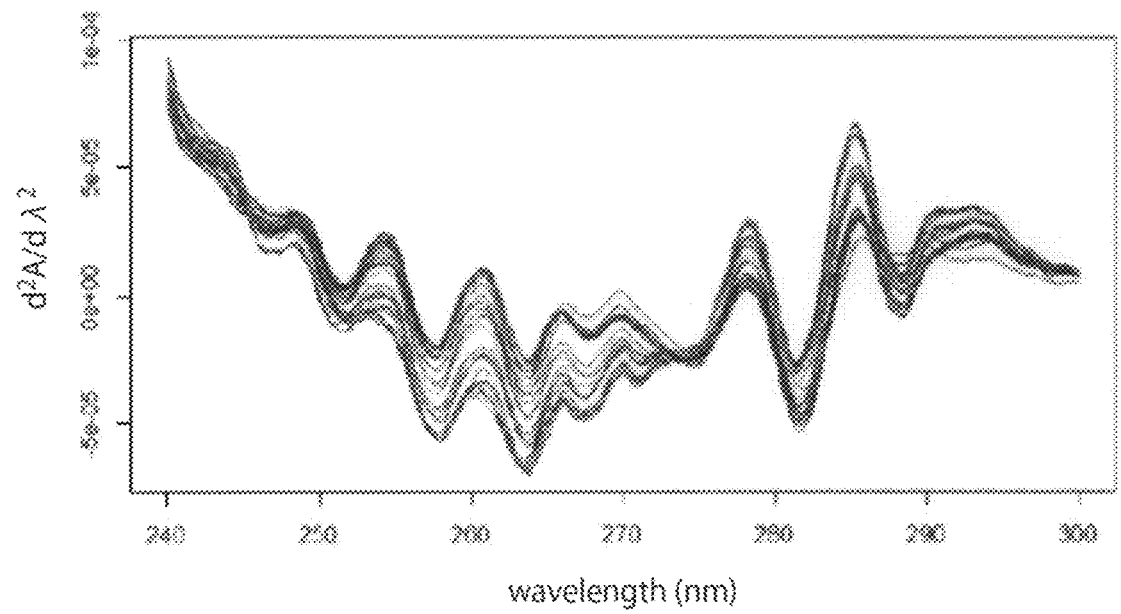

For each of the obtained culture medium samples, a UV spectrum at a wavelength ranging from 240 nm to 300 nm was measured using a UV measurement device (UltraSpec3300pro, GE Healthcare), and R version 3.1.3 (http://www.r-project.org/) was used to perform secondary differential processing. The obtained UV spectrum was as shown in FIG. 4A, and the results of performing the secondary differential processing was as shown in FIG. 4B. Specifically, FIG. 4A shows the results of UV measurement on days 0 to 7 of the control cell culture medium, the ectodermal-differentiated cell culture medium, the mesodermal-differentiated cell culture medium, and the endodermal-differentiated cell culture medium together, and FIG. 4B shows the results of performing the secondary differential processing thereof.

[LC-MS Measurement of Target Metabolite (Hypoxanthine)]

For each of the obtained culture medium samples, the hypoxanthine concentration was measured by LC-MS measurement according to the following procedures.

To 100 μL of each of the samples, 20 μL of 0.5 mM aqueous isopropylmalic acid solution was added as an internal standard substance, and they were mixed. Then, 200 μL of acetonitrile was added to remove proteins. Thereafter, the sample was centrifuged (15,000 rpm, room temperature, 15 minutes) to collect a supernatant. The supernatant was diluted 10 fold with ultrapure water (Milli-Q (registered trademark) water, Merck Co., Ltd.), and the diluted product was analyzed by LC-MS. The LC-MS analysis was performed according to the analysis conditions contained in the "LC/MS/MS Method Package, Cell Culture Profiling" (hereinafter abbreviated as "MP") manufactured by Shimadzu Corporation. MP is a collection of analysis condition parameters for analyzing compounds contained in a medium and a metabolite secreted from cells by LC-MS. The compounds were identified based on the standards that the difference between the retention time of the standard products registered in the MP and the retention time of the compounds in the sample was within ±0.3 minutes, and that both the peaks of target ions and qualifier ions had been detected, and that the intensity value was 1,000 or more. The compounds were quantified by a method of calculating the area in the mass chromatogram for the ions (target ions) characteristic of each compound in the sample.

Figure 5:
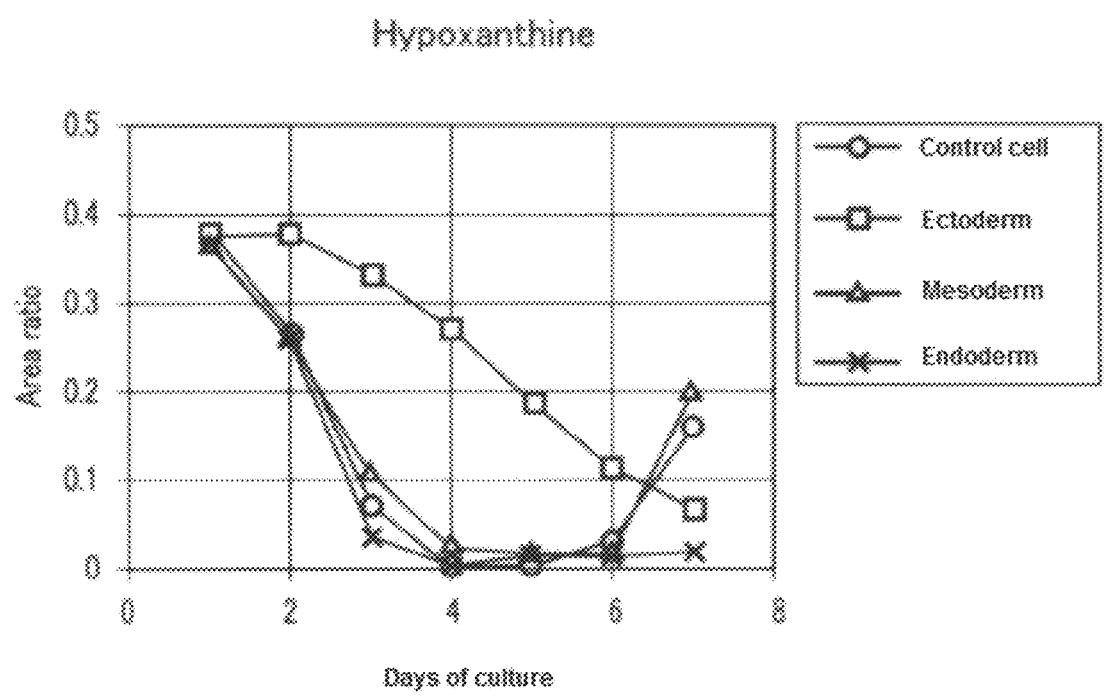
FIG. 5 is a graph showing the results of LC-MS measurement of the hypoxanthine concentration of each of the culture media obtained in the Example of one embodiment of the present disclosure.

The results of the obtained hypoxanthine concentration were as shown in FIG. 5.

[Model Analysis by PLS Method]

With the obtained UV spectrum data defined as an explanatory variable, and hypoxanthine as an objective variable, R version 3.1.3 (https://www.r-project.org/) was used to create two models by PLS-R (Partial Least Squares Regression): A) a model created using only samples on day 1 to day 7 of culture of the control cells and B) a model created using samples on day 1 to day 7 of culture of the target cells and the cells induced into the respective germ layers.

Figure 6:
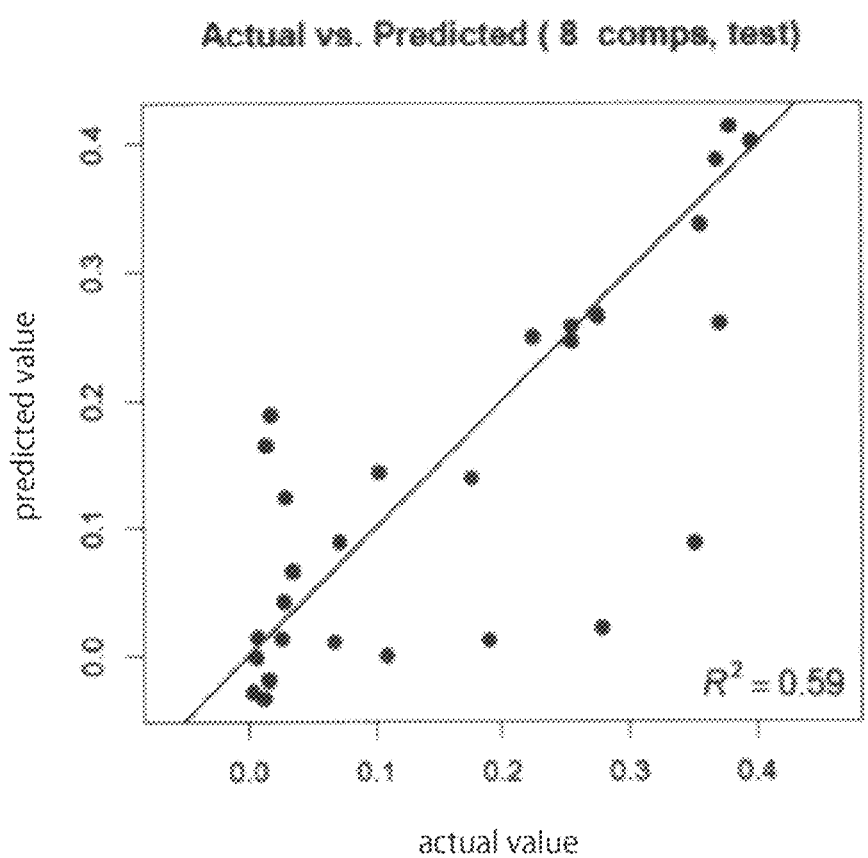
FIG. 6 is a graph showing a coefficient of determination for predicted values and actual measured values in a PLA-R analytic model created using only samples on day 1 to day 7 of culture of control cells in the Example of one embodiment of the present disclosure.
Figure 7:
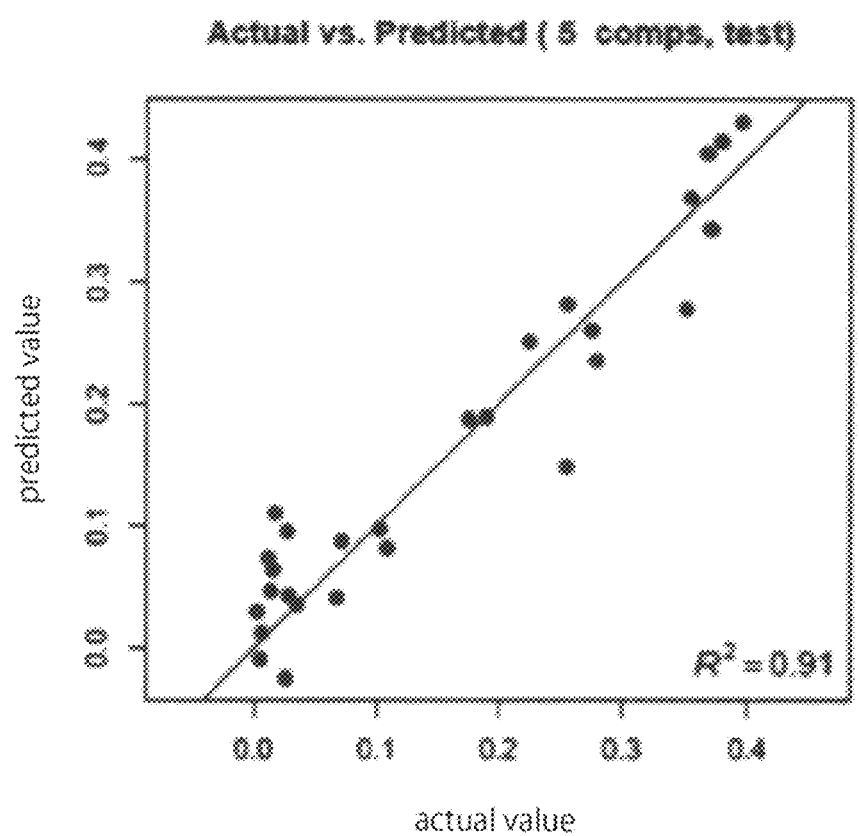
FIG. 7 is a graph showing a coefficient of determination for predicted values and actual measured values in a PLA-R analytic model created using only samples on day 1 to day 7 of culture of target cells and cells induced into the respective germ layers in the Example of one embodiment of the present disclosure.

The predicted value correlation diagram obtained in A was as shown in FIG. 6, and the predicted value correlation diagram obtained in B was as shown in FIG. 7. In FIGS. 6 and 7, the vertical axis indicates the predicted value, and the horizontal axis indicates the actual measured value. Using the analytic models obtained by the PLS analysis, the amount of each biochemical substance could be predicted with high accuracy. The coefficient of determination for the predicted values and the actual measured values was 0.59 in FIG. 6, whereas the coefficient of determination was 0.91 in the model in FIG. 7. A significant improvement was observed.

Figure 8:
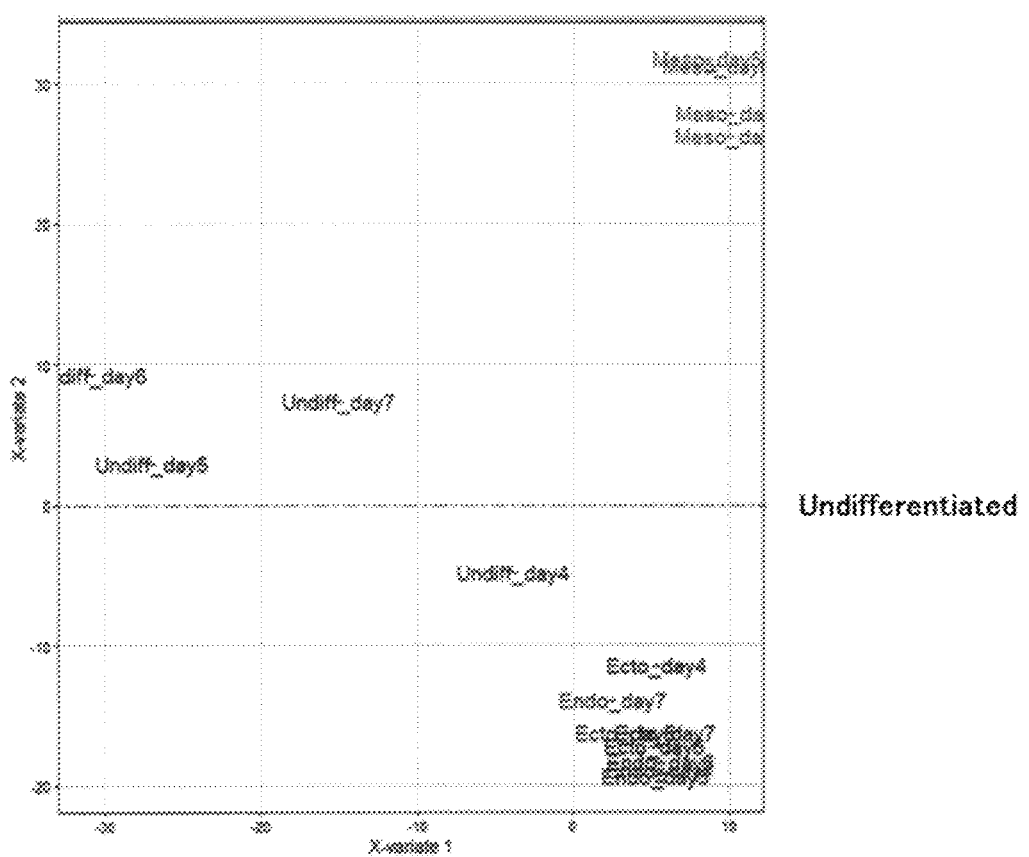
FIG. 8 is a graph obtained when creating a PLA discriminant analysis (PLA-DA) model based on data obtained in an experiment associated with one embodiment of the present disclosure.

Also, as shown in FIG. 8, a PLA discriminant analysis (PLA-DA) model was created based on the data on day 4 to day 7 of culture obtained in this experiment. The PLA-DA model shows that the undifferentiated state of pluripotent stem cells can be monitored only from the spectroscopic information on the culture medium.

REFERENCE SIGNS LIST

1. Cell culture device
2. Irradiation unit
3. Detection unit
4. Control unit
5. Input unit
6. Output unit
7. Data analysis unit
8. Light source
9. Sample
10. Spectroscope
11. Main storage unit
12. Auxiliary storage unit
13. Arithmetic processing unit

The invention claimed is:

1. A method for determining the undifferentiated state of pluripotent stem cells, comprising the steps of:
   irradiating a test culture medium in which pluripotent stem cells have been cultured with wavelength light having a wavelength in the range of 190 nm to 2,500 nm or a partial range thereof, and detecting the reflected light, transmitted light or transmitted reflected light thereof; and
   creating an absorbance spectrum data profile and
   analyzing the absorbance at all or part of the measurement wavelengths in the absorbance spectrum data profile to determine the undifferentiated state of the pluripotent stem cells, based on a comparison to an analytic model created in advance using a plurality of types of control culture media used to culture pluripotent stem cells,
   wherein the plurality of types of control culture media comprise:
   a medium used to maintain the undifferentiated state of the pluripotent stem cells; and
   at least one type of differentiation-inducing medium selected from the group consisting of a medium in which the differentiation into ectodermal cells is induced, a medium in which the differentiation into mesodermal cells is induced, and a medium in which the differentiation into endodermal cells is induced.

2. The method according to claim 1, wherein the differentiation-inducing media comprises the medium in which the differentiation into ectodermal cells is induced, the medium in which the differentiation into mesodermal cells is induced, and the medium in which the differentiation into endodermal cells is induced.

3. The method according to claim 1, wherein the medium for inducing differentiation into ectodermal cells comprises at least one factor selected from the group consisting of: SB431542, Noggin, Dorsomorphin, CKI-7 and VEGF.

4. The method according to claim 1, wherein the medium in which the differentiation into mesodermal cells is induced comprises at least one factor selected from the group consisting of BMP4, retinoic acid and SCF.

5. The method according to claim 1, wherein the medium in which the differentiation into endodermal cells is induced comprises at least one factor selected from the group consisting of Activin-A, Wnt-3a, BMP4, CHIR99021 and Wortmannin.

6. The method according to claim 1, which is a method for noninvasively determining the undifferentiated state of pluripotent stem cells.

7. The method according to claim 1, wherein the analytic model is created using, as objective variables, the contents of an extracellular metabolite in the plurality of types of control culture media.

8. The method according to claim 7, wherein the extracellular metabolite is at least one selected from the group consisting of L-glutamic acid, L-alanine, ammonia, ornithine, 2-aminoadipic acid, deoxycytidine, glutamic acid, tryptophan, aspartic acid, alanine, cystine, hypoxanthine, uridine, 2-hydroxybutyric acid, 2-hydroxyvaleric acid, 3-hydroxyvaleric acid, 2-hydroxyisovaleric acid, 3-hydroxyisovaleric acid, urea, 4-hydroxybenzoic acid, 4-aminobenzoic acid and ribonic acid.

9. The method according to claim 1, wherein the analytic model is created by regression analysis that is a PLS method.

10. The method according to claim 1, wherein the test culture medium and the control culture media are used culture media which have been replaced by medium replacement.

11. The method according to claim 10, wherein the time period of the medium replacement is 24 to 48 hours.

12. A method for subculturing pluripotent stem cells, comprising the steps of:
   conducting the determination method according to claim 1,
   collecting the pluripotent stem cells determined to be undifferentiated cells by the determination method according to claim 1, as cells necessary for subculture; and
   removing the pluripotent stem cells determined to be cells that have started to differentiate by the determination method according to claim 1, as cells unnecessary for culture and/or subculture.

* * * * *